United States Patent [19]

Herrmann et al.

[11] Patent Number: 5,369,119
[45] Date of Patent: Nov. 29, 1994

[54] USE OF IMEXON AS AN IMMUNE SUPPRESSIVE AND PHARMACEUTICAL COMPOSITIONS CONTAINING IMEXON

[75] Inventors: Dieter Herrmann, Heidelberg; Rainer Haag, Ladenburg; Elmar Bosies, Weinheim; Uwe Bicker, Bensheim; Wolfgang Kampe, Heddesheim, all of Germany

[73] Assignee: Boehringer Mannheim GmbH, Mannheim, Germany

[21] Appl. No.: 26,210

[22] Filed: Mar. 2, 1993

Related U.S. Application Data

[60] Division of Ser. No. 759,204, Sep. 11, 1991, abandoned, which is a division of Ser. No. 617,301, Nov. 20, 1990, abandoned, which is a continuation of Ser. No. 385,920, Jul. 27, 1989, abandoned.

[30] Foreign Application Priority Data

Oct. 5, 1989 [DE] Germany ............... 3825667

[51] Int. Cl.$^5$ ........................... A61K 31/415
[52] U.S. Cl. ................... 514/389; 514/885; 514/50
[58] Field of Search ........................... 514/50

[56] References Cited

U.S. PATENT DOCUMENTS

| | | | |
|---|---|---|---|
| 4,083,987 | 4/1978 | Bicker et al. | 424/273 |
| 4,996,219 | 2/1991 | Tsaklakidis | 514/341 |
| 5,055,290 | 10/1991 | Bicker et al. | 514/340 |

FOREIGN PATENT DOCUMENTS 2528460 1/1977 Germany.
1573730 8/1980 United Kingdom.

OTHER PUBLICATIONS

Fortschritt Med 105, 509–512 Bicker et al 1987.
ICRS, 5, p. 428 Bicker et al 1977.
Immunol. Ser. 25, 447–473 Bicker 1984.
Cancer Treatment Symp. 1, 27–35, Micksche et al. 1985.
Fortschritt Med. 96, 681–684 Bicker 1978.
Experimental Investigations on Increased Resistance to Candida Albians and Staphylococcus . . . Ziegler et al Chem. Abst. 164124m 88, 1978.
BM 06002 a New Immunostimulating Compound, Bicker, Chem. Ast. 70900e 89, 1978.
Modulation in vitro of Immune Parameters in Homosexual Males . . . Patt et al J. Biol. Resp. Modified 5, 263–269, 1986.
Immunopharmacol. Immunotoxicol. 1990, 12, 1–21; Chirigos et al.
Proceedings of AACR, 1985, 26, 281; Patt et al.
Fortschritt Med. 1978, 96, 681–684; Bicker.

*Primary Examiner*—G. S. Kishore
*Attorney, Agent, or Firm*—Nikaido, Marmelstein, Murray & Oram

[57] ABSTRACT

The subject of the present invention is the use of imexon for the production of pharmaceutical compositions with an immunosuppressive action. The present invention also provides pharmaceutical compositions containing imexon and further active materials.

13 Claims, No Drawings

USE OF IMEXON AS AN IMMUNE SUPPRESSIVE AND PHARMACEUTICAL COMPOSITIONS CONTAINING IMEXON

This application is a division of application Ser. No. 07/759,204 filed Sep. 11, 1991, now abandoned, which is a divisional Ser. No. of 617,301 filed Nov. 20, 1990; now abandoned, which is a continuation of Ser. No. 385,920 filed Jul. 27, 1989; now abandoned.

The present invention is concerned with the use of imexon for the preparation of pharmaceutical compositions with an immunosuppressive action and is also concerned with pharmaceutical compositions containing imexon in combination with a further active material.

In particular, the present invention is concerned with the use of imexon for the preparation of pharmaceutical compositions for the treatment of autoimmune diseases, B cell and plasma cell neoplasias, lymphoblastic lymphomas, rejection reactions after tissue and organ transplants and viral and retroviral infections, for example AIDS or ARC (AIDS-related complex). In general, imexon can be used for the treatment of diseases in which a pathophysiologically increased B-lymphocyte proliferation or B-lymphocyte activation is to be observed.

Imexon, which has the systematic designation 4-imino-1,3-diazabicyclo-(3.1.0)-hexan-2-one, has the following structural formula:

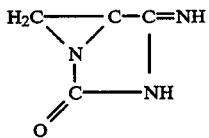

With regard to its structure, imexon is not comparable with any other active compounds used therapeutically. The surprisingly found preferred action on B-lymphocutes also has no parallel with other previously known immunosuppressively-acting compounds.

Imexon and processes for the preparation thereof are known from U.S. Pat. No. 4,083,987. The compound is thereby described as being a cancerostatically-active therapeutic which displays immune-stimulating properties. The cancerostatic action was demonstrated on the basis of the inhibition of the tumour growth of Walker sarcoma 256 after the administration of imexon to rats. The immune-stimulating action can be deduced from experiments in which an increase of the leukocytes, as well as an increase of the number of the antibody-forming spleen cells could be observed after the administration of imexon. The pharmacological importance of imexon is, according to this U.S. Patent Specification, to be seen in the fact that imexon so strongly impairs the growth of the rapidly dividing cancer cells that, under certain circumstances, a regression of the tumours is possible. According to U.S. Pat. No. 4,083,987, the advantageous action of imexon lies in the simultaneous strengthening of the weakened immune defence system inherent in the body which accompanies the cancerostatic action.

In general, immune suppressives as such have been known for a long time from the prior art (Pharmazie unserer Zeil, 1, 2-8/1972 and 12, 20-29/1983). The expression "immune suppression" used in this connection generally designates the various types of non-specific suppression of the immune response, for example with the help of antisera, ionising irradiations and special therapeutics.

The use of immune suppressive-acting chemotherapeutics can be employed after the transplantation of tissue or organs and in the therapy of autoimmune diseases. They inhibit the proliferation of lymphocytes by direct or indirect intervention into the synthesis of DNA or RNA. To this class of compounds belong cyclosporins, folic acid antagonists, purine analogues, alkylating compounds, such as cyclophosphamide, and certain corticosteroids. However, a disadvantage of these previously used immunosuppressives is the increased extent of observed susceptibility to infection of the treated organism which weakens the whole of the body's immune system and suppresses not only the humoral but also the cellular immune response.

The previously known artificially induced immune suppression could be achieved in various ways: by the administration of antigens, administration of specific antisera or antibodies, the use of other biological reagents, for example antilymphocyte antisera, by the use of immunosuppressively-active compounds, by radiation or by the surgical removal of lymphoid tissue.

The immunosuppressive properties of the immunosuppressives at present known, for example cytostatics and corticosteroids, are dosage-dependent but nonselective, i.e. they act upon all immune-competent cells. These compounds inhibit not only the humoral but also the cellular immune response to a plurality of antigens and act non-specifically on T- and B-lymphocytes. Cyclosporin A, which at present is the most selective medicament, suppresses not only the proliferation of T-lymphocytes but also immune processes which are not T-cell-dependent.

Therefore, there is a great interest for immunosuppressives which interfere specifically with pathologically strengthened or increased immune mechanisms but without influencing the immune reactions which take place normally in the body. Hitherto, such specifically-active immunosuppressive substances are not known.

Therefore, it is an object of the present invention to provide such a new immunosuppressively-active agent.

Suprisingly, we have now found that imexon solves this problem and can be used as an advantageous immune suppressive. It specifically suppresses the B-cell proliferation or the B-cell activation. It can be advantageously used in the treatment of all diseases in which a polyclonal activation or proliferation of B-cells is of pathophysiological, symptomatic or clinical relevance.

In this sense, the treatment of the following diseases can, for example, be considered: autoimmune diseases, for example rheumatoid arthritis, diabetes mellitus Type I, psoriasis, lupus systemicus erythematosus; rejection reactions after tissue or organ transplants, for example of skin, bone marrow and kidneys; viral or retroviral infections of any genesis, for example ARC (AIDS-related complex) and AIDS, as well as their preliminary stages; B-cell leukaemias and lymphomas, for example chronic lymphatic leukaemia, lymphoblastic lymphoma, for example Burkitt's lymphoma and the like, or B-cell/plasma cell neoplasias, for example plasmacytoma (multiple myeloma).

As autoimmune diseases, in the literature there are generally designated those diseases in which the formation of autoantibodies have a pathogenic significance.

These autoantibodies are directed against the body's own antigens and thus bring about a destruction of the body's own organs, cells or proteins. It is an object to suppress these diseased overreactions of the immune system with specifically-acting immune suppressives.

Furthermore, we have, surprisingly, found that imexon inhibits the proliferation of B-lymphocytes in a dosage-dependent manner.

Thus, according to the present invention, imexon specifically suppresses pathological B-cell proliferation or B-cell activation, and this is accomplished without adverse influence on T-cell proliferation or activation.

Imexon can be used itself directly or in the form of physiologically acceptable addition salts.

In the meaning of the present invention, the expression "immune suppression" is, in general, to comprise all aspects of the naturally-induced immunological non-responsiveness, artificially-induced non-responsiveness and pathologically-induced tolerance to auto- and foreign antigens.

The immune suppressive action of imexon could be demonstrated on the basis of the inhibition of the proliferation of human B-lymphocytes, the proliferation being induced experimentally by the B-cell growth factor (BCGF).

Furthermore, the pharmacological properties of imexon could be characterised by concanavalin A (ConA)-induced proliferation of murine splenocytes (LTT), by phythaemagglutinin (PHA)-induced proliferation of human lymphocytes, as well as by tumour growth inhibition assay (TGI).

In order to stimulate dormant B-cells to proliferation, two signals are necessary. The first signal is an activation signal which is brought about by an antigen or anti-$\mu$. The transmission of this activating signal finally has the result that receptors for the B-cell growth factor (BCGF) are expressed on the B-cell surface. BCGF is a soluble lymphokine secreted by T-cells with a molecular weight of 17,000 to 18,000 D. The expression of BCGF receptors on the B-cells makes it possible for these to respond to the proliferation signal of BCGF. Normally, B-cells are converted by this two-signal process from the dormant state into the proliferative phase.

Imexon now suppresses this procedure specifically insofar as the concanavalin A (ConA)- and phytohaemagglutinin (PHA)-induced lymphocyte proliferation, as well as the spontaneous proliferation of methylcholanthrene-induced fibrosarcoma cells (MethA), are not influenced or only in the case of 10 to 30 times higher concentrations.

The antiretroviral action of imexon could be demonstrated on the basis of the Rauscher virus leukaemia model (cf. Example 5). The influence of imexon on the spontaneous formation of lymphomas and the synthesis of antinuclear autoantibodies in the mouse (Example 6) proves the effectiveness on an animal model for autoimmune diseases.

Imexon can also be used as a combination preparation with other immune suppressives, for example cyclosporin A, ciamexon or azathioprine, as well as antiretrovirally-active substances, for example azidothymidine (AZT).

A combination of imexon with cytostatics is also possible, for example with cis-platinum complexes, such as cis-diaminodichloroplatinum, or with adriamycin, cyclophosphamide, vincristin, tamoxifen, methotrexate or 5-fluorouracil and the like. In this connection, the use of such combination preparations is of especial interest subsequent to a plasmaphaeresis for the monitoring of autoimmune diseases.

In the case of the use of a combination therapy, it is possible to administer the active materials in a so-called fixed combination, i.e. in a single pharmaceutical formulation, in which both active materials are present simultaneously, or to use a so-called free combination in which the active materials are administered in the form of pharmaceutical formulations simultaneously or also successively in individually selectable dosage relationships.

For the preparation of pharmaceutical agents, imexon is mixed in known manner with appropriate pharmaceutical carrier substances, possibly granulated and pressed, for example, into tablets or dragee cores. A filling of the mixture into hard capsules is also possible. With the addition of appropriate adjuvants, a solution or suspension in water, an oil, for example olive oil, or a high molecular weight polymer, for example polyethylene glycol, can also be produced and administered in the form of injection solutions, soft gelatine capsules, syrups or drops.

As solid carrier materials, there can be used, for example, starches or starch derivatives, sugars, sugar alcohols, celluloses or cellulose derivatives, tenside, talc, highly dispersed silicic acids, high molecular weight fatty acids or the salts thereof, gelatine, agar-agar, calcium phosphate, animal or vegetable fats or waxes and solid high molecular weight polymers (such as polyethylene glycols or polyvinylpyrolidones). Compositions suitable for oral administration can, if desired, contain flavouring and sweetening materials.

The dosage of the active material imexon depends upon the age and sex of the individual, as well as upon the nature of the indications to be treated.

In principle, the treatment can be based on the fact that 0.1 to 100 mg. of imexon per kg. body weight can be administered daily orally, intravenously, subcutaneously or intramuscularly. However, it is preferred to use amounts of from 5 to 50 mg./kg. body weight and especially 5 to 20 mg./kg. body weight. The dosages of the active material can be administered 1 to 3 times daily.

The specific immunosuppressive action of imexon is demonstrated by the following Examples:

EXAMPLE 1

BCGF-dependent proliferation of human B-lymphocytes.

The enrichment of peripheral human B-cells and the BCGF proliferation assay were carried out as follows (Cf. Eur. J. Immun., 16, 350/1986):

Enriched human B-lymphocytes were washed twice with complete RPMI 1640 medium (streptomycin/penicillin, L-glutamine, 2-mercaptoethanol, FCS) and adjusted to $3 \times 10^5$ cells/ml. 160 ml. of this suspension were pipetted into each well of microtitre plates. As pseudoantigen, there were added thereto 10 ml. of a solution of HFC $\mu$S-IgG (300 $\mu$g./ml.) and, as growth factor, 20 $\mu$l. BCGF (Cellular Products Incorporated). To this were pipetted 20 $\mu$l. of the compound to be tested in 10 fold concentration. The cultures were incubated for a total of 140 hours at 37° C. with 5% carbon dioxide and 95% relative atmospheric humidity. 16 hours before the conclusion of the incubation period, each culture was pulsed with 1 $\mu$Ci of a [$^3$H]-thymidine solution. At the end of the experiment, the cells were collected with a harvester and the incorporated radioactivity determined in a liquid scintillation counter.

EXAMPLE 2

Concanavalin A (ConA)-induced proliferation of murine splenocytes

Spleen cells ($4 \times 10^5$) of CB6F$_1$ mice were incubated for a total of 48 hours with 0.5 µg./ml. ConA in microtitre plates (Nunc GmbH, Wiesbaden, Federal Republic of Germany) and various concentrations of imexon in 6 fold batches. 5 hours before the termination of the incubation period, the cultures were pulsed with [$^3$H]-thymidine and subsequently harvested on glass fibre filter platelets by means of a multi-sample harvester (Skatron A. S., Lier, Norway). The filter platelets were dried and the radioactivity was determined in a Packard scintillation spectrometer.

EXAMPLE 3

Phythaemagglutinin (PHA)-induced proliferation of human lymphocytes 1 ml. of human whole blood was diluted with 500 µg. PHA solution (500 µg./ml.) and diluted with 48 ml. DMEM medium. 200 µl. amounts of this batch were mixed with 20 µl. of the imexon concentration to be tested in 6 fold batches and incubated for 4 days. After pulsing with [$^3$H]-thymidine, incubation was continued for a further 24 hours, followed by harvesting and evaluation as described in Example 2.

EXAMPLE 4

Tumour growth inhibition assay (TGI)

A methylcholanthrene-induced fibrosarcoma cell line (MethA) was obtained from our own tumour cell bank and passed intraperitoneally into CB6F$_1$ mice.

$1 \times 10^4$ MethA cells were incubated with the imexon concentration to be tested in DMEM medium for 48 hours. 3 hours before the end of the incubation time, pulsing was carried out with [$^3$H]-thymidine, followed by harvesting and evaluated as described in Example 2.

The values given in the following Table 1 show the results of a representative experiment. They are the results of the investigations with imexon in the TGI, LTT (ConA, PHA) as well as in the BCGF assay, i.e. the influence of imexon on the proliferation of the MethA sarcoma cell, T-lymphocytes and B-cells is shown. Imexon suppressed significantly and specifically the BCGF-induced B-cell proliferation at a concentration of 1 µg./ml., whereas the lymphocyte proliferation induced either by ConA or PHA was only significantly inhibited at concentrations of >10 µg./ml. Furthermore, the spontaneous proliferation of MethA sarcoma cells was also only significantly suppressed at >10 µg./ml.

The results of the above experiments are summarised in the following Table 1:

TABLE 1

Effect of imexon the proliferation of various cell types

| Imexon (µg/ml) | TGI (MethA) $^3$H-TdR cpm (n = 6) $\bar{x}$ | SD | % inhibition | LTT (Splenocytes, ConA) $^3$H-TdR cpm (n = 6) $\bar{x}$ | SD | % inhibition | LTT (Splenocytes, PHA) $^3$H-TdR cpm (n = 6) $\bar{x}$ | SD | % inhibition | BOGF (human B-lymphocytes) $^3$H-TdR cpm (n = 6) $\bar{x}$ | SD | % inhibition |
|---|---|---|---|---|---|---|---|---|---|---|---|---|
| Control | 33966 (n = 5) | 3000 | — | 109879 | 12203 | — | 44283 | 6458 | — | 5541 | 1792 | — |
| 100 | 534 | 363 | 98** | 903 | 62 | 99** | 585 | 44 | 99** | 562 | 44 | 90** |
| 30 | 911 | 110 | 97** | 2509 | 863 | 98** | 573 | 59 | 99** | 617 | 59 | 89** |
| 10 | 21913 | 2357 | 35** | 24895 | 6563 | 77** | 4724 | 704 | 89** | 574 | 50 | 90** |
| 3 | 35473 | 3135 | −4 | 118487 | 9494 | −8 | 35850 | 13018 | 19 | 831 | 231 | 85** |
| 1 | 35475 | 1753 | −4 | 119120 | 9172 | −8 | 49348 | 4168 | −11 | 2096 | 455 | 62* |
| 0.3 | 37593 | 3080 | −11 | 134032 | 37682 | −22 | 45542 | 9870 | −3 | 4201 | 1636 | 24 |
| 0.1 | 31722 | 3991 | 7 | 109717 | 11192 | 0 | 41849 | 1892 | 5 | 4847 | 1146 | 13 |

*p < 0.002
**p < 0.001

EXAMPLE 5

Antiretroviral action of imexon in the Rauscher virus leukaemia model 8 to 9 week old female Balb/c mice were infected with 0.2 ml. of spleen homogenate of infected animals (diluted 1:2 in PBS). From day 0 (or day −1) up to day 13, the animals were treated intraperitoneally daily with the given dosage of the active material. On day 7 and on day 14, animals of the individual treatment groups were sacrificed and the spleen weight determined as a measure of the viraemia.

In the following Table 2 are summarised the results of the investigations. Imexon controlled the virus-caused increased weight of the spleen in the same dosage range as azidothymidine.

TABLE 2

Results of a comparative investigation of the action of imexon and azidothymidine (AZT) in the Rauscher virus leukaemia model. There are given average values and standard deviations of 5 or 10 fold determinations (Experiment R 17)

| | placebo (−Virus) | placebo (+Virus) | Imexon 90 | Imexon 120 | AZT 100 | Ribavirin 100 |
|---|---|---|---|---|---|---|
| day 7 | | | | | | |
| spleen weight (g) | 0.112 ± 0.019 (5) | 0.091 ± 0.045 (10) | 0.248 ± 0.030 (10) | 0.190 ± 0.031 (10) | 0.185 ± 0.017 (10) | 0.116 ± 0.012 (10) |
| animal weight (g) | 20.2 ± 1.1 (5) | 20.7 ± 1.3 (10) | 21.4 ± 1.7 (10) | 20.0 ± 1.4 (10) | 20.0 ± 0.8 (10) | 18.8 ± 1.2 (10) |
| day 14 | | | | | | |
| spleen weight (g) | 0.165 ± 0.013 (5) | 0.670 ± 0.201 (10) | 0.306 ± 0.121 (10) | 0.238 ± 0.076 (10) | 0.316 ± 0.089 (10) | 0.260 ± 0.060 (7)* |

TABLE 2-continued

Results of a comparative investigation of the action of imexon and azidothymidine (AZT) in the Rauscher virus leukaemia model. There are given average values and standard deviations of 5 or 10 fold determinations (Experiment R 17)

| | placebo (−Virus) | placebo (+Virus) | dose (mg/kg × d, i.p.) | | | |
|---|---|---|---|---|---|---|
| | | | Imexon 90 | Imexon 120 | AZT 100 | Ribavirin 100 |
| animal weight (g) | 20.5 ± 0.3 (5) | 19.6 ± 0.9 (10) | 19.6 ± 1.9 (10) | 20.9 ± 0.8 (10) | 20.9 ± 1.1 (10) | 19.2 ± 1.1 (7)* |

*3 animals died because of toxicity

EXAMPLE 6

Action of imexon in the case of autoimmune diseases

With increasing age, the mouse strain MRL 1pr/1pr develops increasingly spontaneously lymphadenoma and SLE-like symptoms, for example the synthesis of anti-nuclear autoantibodies. For the investigation of the prophylactic effect of imexon on the development of these symptoms, 11 week old MRL mice were treated intraperitoneally once daily with the given dosages of imexon and cyclophosphamide. The number of lymphadenomas and the concentration of antinuclear antibodies were documented. In the case of the investigation of the therapeutic potency of imexon, MRL mice, after each animal had developed at least one lymphadenoma (about 14 week old animals), were also treated once daily with the given dosages of imexon and cyclophosphamide. The measurment parameters were again the number of lymphadenomas, as well as the autoantibody titre.

The results of these investigations have shown that imexon, in the case of very good compatibility, lowers the number of spontaneously arising lymphadenomas and the concentration of DNA-specific antibodies. The effectiveness of imexon was also shown in the case of therapeutic use with animals already having lymphomas. The number of lymphadenomas decreased dependent upon the dosage, as well as the titre of the autoantibodies.

EXAMPLE 7

Preparation of a pharmaceutical formulation of imexon

A film tablet with, for example, 100 g. of active material and which has the following composition has proved to be an appropriate pharmaceutical composition:

| | weight/unit/mg. |
|---|---|
| imexon | 100.000 |
| lactose monohydrate | 63.000 |
| poly-(0-carboxymethyl)-starch, sodium salt | 7.000 |
| poly-(1-vinyl-2-pyrrolidone) 25,000 | 4.000 |
| poly-(0-carboxymethyl)-starch, sodium salt | 3.000 |
| microcrystalline cellulose | 20.000 |
| highly dispersed silicon dioxide | 1.500 |
| magnesium stearate | 1.500 |
| core weight | 200.000 |

The film tablets were then produced in the usual way by the film drageeing of the imexon cores obtained.

Film tablets with, for example 10 mg., 50 mg., 200 mg. and 500 mg. of active material were produced in a corresponding manner.

We claim:

1. A method of suppressing B-cell proliferation or activation caused by AIDS or ARC, or involved in a B-cell lymphoma or B-cell leukemia, in a patient, said method comprising administering to said patient a B-cell proliferation or activation suppressing amount of Imexon or physiologically acceptable salt thereof.

2. Method of claim 1, wherein the B-cell activation or proliferation suppression is accomplished without suppression of T-cell proliferation or activation.

3. Method of claim 1, wherein the patient is administered about 10 to 1000 mg of Imexon or salt thereof per administration.

4. Method of claim 1, wherein the patient is administered an amount of from 0.1 to 1000 mg/kg of patient body weight of Imexon or salt thereof per administration.

5. Method of claim 4, wherein the amount is 5 to 50 mg/kg body weight.

6. Method of claim 5, wherein the amount is 5 to 20 mg/kg body weight.

7. Method of claim 1, wherein the disease is AIDS or ARC.

8. Method of claim 7, wherein azidothymidine (AZT) in an effective amount is also administered to the patient.

9. Method of claim 1, wherein the Imexon is used as a combination preparation with at least one other anti virally-active substance.

10. Method of claim 1, wherein Imexon or salt thereof is administered to said patient orally, intravenously, subcutaneously or intramuscularly.

11. Method of claim 7, wherein the patient also has a condition selected from the group consisting of B-cell leukemia, B-cell lymphoma, B-cell neoplasia and B-cell plasma cell neoplasia.

12. A method of suppressing B-cell proliferation or activation caused by AIDS or ARC, in a patient, said method comprising administering to said patient a B-cell proliferation or activation suppressing amount of Imexon or physiologically acceptable salt thereof.

13. A method of suppressing B-cell proliferation or activation involved in a B-cell lymphoma or B-cell leukemia, in a patient, said method comprising administering to said patient a B-cell proliferation or activation suppressing amount of Imexon or physiologically acceptable salt thereof.

* * * * *